March 27, 1956 E. S. BOERNER Plant Pat. 1,466
CHRYSANTHEMUM PLANT
Filed April 15, 1955
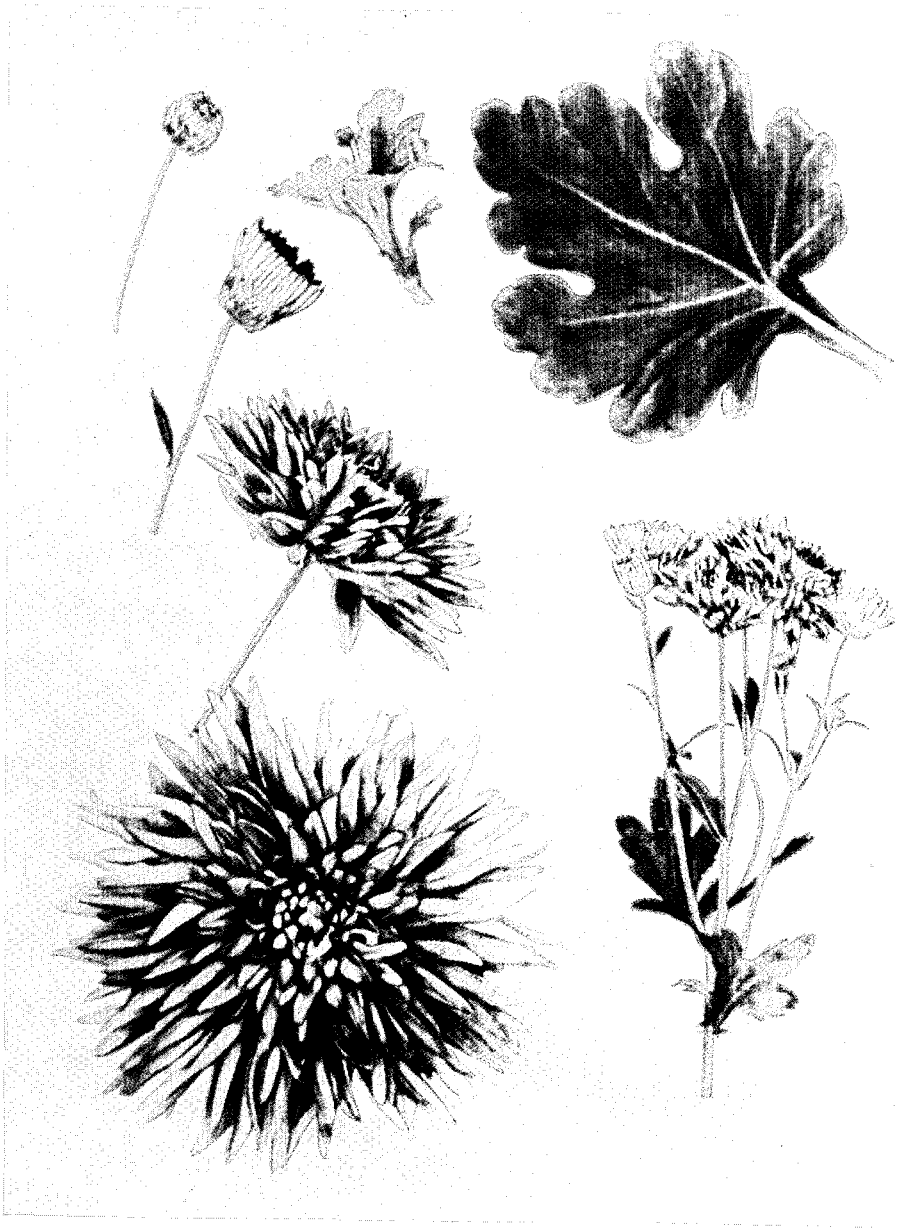
Inventor.
E. S. Boerner
By: Robb & Robb
Attorneys.

United States Patent Office

Plant Pat. 1,466
Patented Mar. 27, 1956

1,466

CHRYSANTHEMUM PLANT

Eugene S. Boerner, Newark, N. Y., assignor to Jackson & Perkins Company, Newark, N. Y., a corporation of New York Application April 15, 1955, Serial No. 501,758

1 Claim. (Cl. 47—60)

The present invention relates to a new and distinct variety of chrysanthemum plant of the decorative class, which was originated by me by crossing an unnamed and unpatented deep pink chrysanthemum Rubellum seedling with the variety "Grosbeak" (Plant Patent No. 1,132).

The primary objective in making this cross was to obtain a larger-flowered double-red chrysanthemum variety of the decorative class in the hardy garden Rubellum series of chrysanthemums. This objective was fully achieved, as evidenced by the fact that my new variety is particularly characterized by the distinctive color of the flowers as hereinafter more fully described, the relatively large size of the flowers and the early-blooming habit thereof, the hardiness of the plant and the good frost resistance of the buds and flowers. These features definitely distinguish my new variety from its parents, as well as from all other varieties of its class of which I am aware.

Asexual reproduction of my new variety by top cuttings and by underground runners, as performed by me at Newark, New York, shows that the foregoing characteristics and distinctions come true to form and are established and transmitted through succeeding propagations.

The accompanying drawing shows typical specimens of the vegetative growth and the flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: An unnamed deep pink chrysanthemum Rubellum seedling × "Grosbeak."
Classification: Decorative.
Growth: From 24 inches to 30 inches.
Cold resistance: Very hardy; flowers are frost-resistant in Northern New York.

Blooming period: In the Newark, New York, climatic area, blooming starts about September 20 and continues to make a good showing until frost.

FLOWERS (Observations made from specimens grown in a field at Newark, New York, in the early morning in about mid-October.)

Bud:
*Color.*—When sepals first divide—Magenta, Plate 26. When petals begin to unfurl—Indian Lake, Plate 26. When half blown: inside of petals—Bordeaux, Plate 12; reverse of petals—Indian Lake, Plate 26, lightly overcast with Tyrian Pink, Plate 12.
*Peduncle.*—Strength—strong. Color—Cress Green, Plate 31.

Bloom:
*Size.*—From 4 inches to 4½ inches.
*Stem.*—Strong.
*Form.*—Decorative.
*Petalage.*—Double; tubular.
*Color.*—Center of flower—Rosolane Purple, Plate 26, lightly overcast with Amaranth Pink, Plate 12. Outer petals—Rosolane Purple, Plate 26, lightly overcast with Light Rosolane Purple, Plate 26. Base of petals—Clear Dull Green-Yellow, Plate 17. Inside of petals—Amaranth Purple, Plate 12, lightly overcast with Pomegranate Purple, Plate 12. Reverse of petals—Light Rosolane Purple, Plate 26, lightly overcast with Pale Amaranth Pink, Plate 12.
*Petals.*—Texture—medium. Form—Long; tubular.
*Fragrance.*—Characteristic chrysanthemum.

PLANT

Form: Upright; bushy.
Growth: Very free.
Foliage:
*Size.*—Large.
*Quantity.*—Normal.
*Color.*—Upper side—Forest Green, Plate 17. Reverse side—Light Elm Green, Plate 17.
*Texture.*—Leathery; thick.

I claim:

A new and distinct variety of chrysanthemum plant of the decorative type, substantially as herein shown and described, characterized particularly as to novelty by its early-blooming habit, the relatively large size and distinctive color of its flowers, its hardiness, and the good frost resistance of its buds and open flowers.

No references cited.